(12) United States Patent
Richmond

(10) Patent No.: US 10,537,300 B2
(45) Date of Patent: Jan. 21, 2020

(54) HEAD MOUNTED MICROPHONE ARRAY FOR TINNITUS DIAGNOSIS

(71) Applicant: Wisconsin Alumni Research Foundation, Madison, WI (US)

(72) Inventor: Burke S. Richmond, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 322 days.

(21) Appl. No.: 15/137,174

(22) Filed: Apr. 25, 2016

(65) Prior Publication Data

US 2017/0303887 A1 Oct. 26, 2017

(51) Int. Cl.
*A61B 7/00* (2006.01)
*H04R 3/00* (2006.01)
*A61B 5/00* (2006.01)

(52) U.S. Cl.
CPC ............ *A61B 7/001* (2013.01); *A61B 5/6814* (2013.01); *A61B 5/6822* (2013.01); *A61B 5/7275* (2013.01); *A61B 5/742* (2013.01); *H04R 3/005* (2013.01); *A61B 2562/04* (2013.01)

(58) Field of Classification Search
CPC ... A61B 5/6814; A61B 5/6822; A61B 5/7275; A61B 5/742; A61B 7/001
See application file for complete search history.

(56) References Cited

U.S. PATENT DOCUMENTS

| 4,226,248 A | 10/1980 | Manoli |
| 4,928,705 A * | 5/1990 | Sekhar .................... A61B 7/001 600/586 |
| 8,419,652 B2 | 4/2013 | Rajamani et al. |
| 8,475,396 B2 | 7/2013 | Jones et al. |
| 2007/0113649 A1* | 5/2007 | Bharti .................. A61B 5/4818 73/431 |
| 2009/0012430 A1* | 1/2009 | Lovoi ................ A61B 5/02007 600/586 |
| 2012/0283593 A1* | 11/2012 | Searchfield ............ H04R 25/75 600/559 |

* cited by examiner

*Primary Examiner* — Patrick Fernandes
(74) *Attorney, Agent, or Firm* — Boyle Fredrickson S.C.

(57) ABSTRACT

A three-dimensional, head mounted microphone array is employed to isolate and analyze intracranial sound sources such as may provide for objective tinnitus. The microphone array allows a region of interest within the patient's head to be isolated for the detection of sounds and allows episodic sounds to be automatically identified as to location. An interactive display allows a better understanding of sound locations and the extracted sounds can be analyzed with respect to a library of sounds linked to particular locations and diagnoses.

21 Claims, 2 Drawing Sheets

HEAD MOUNTED MICROPHONE ARRAY FOR TINNITUS DIAGNOSIS

STATEMENT REGARDING FEDERALLY SPONSORED RESEARCH OR DEVELOPMENT

CROSS REFERENCE TO RELATED APPLICATION

BACKGROUND OF THE INVENTION

The present invention relates to a clinical apparatus for noninvasive investigation of sounds genera led in the human head (for example, in objective tinnitus) and in particular to a system for providing improved isolation and localization of such intracranial sounds.

Tinnitus is a perception of noise in the ears, such as ringing or pulsing that has no external source. The most common type of tinnitus is subjective tinnitus in which the patient hears sounds that is neural in origin and can only be heard by the patient. Subjective tinnitus can be the result of nerve or hair eel) damage in the inner ear or the central nervous system.

Objective tinnitus is a result of an acoustic sound source in the head or propagated from other parts of the body that, in theory, could be audible to an external observer. Subjective tinnitus can not be conventionally imaged, and even with advanced techniques subtypes are not quantifiable: likewise, objective tinnitus has many subtypes though there is no standardized method to quantify and categorize subtypes. Although objective tinnitus accounts for less than five percent of overall tinnitus cases, it can reflect a broad array of medical conditions. Some are life threatening and others can be confused with subjective tinnitus or be source of psychological distress. In cases where objective tinnitus is a result of vascular or neuromuscular disorders, such confusion can prevent a timely evaluation of these disorders, while in cases of more benign mechanisms, the inability to quantify the symptom can result in ongoing behavioral distress.

SUMMARY OF THE INVENTION

The present invention provides a head mounted microphone array permitting sophisticated signal processing to be applied to the detection and evaluation of sound sources within the head. As such, the apparatus may be used to positively identify objective tinnitus or other similar symptoms and to characterize the detected sound with respect to possible clinical conditions, for example, intracranial vascular pathologies or the like. By providing a three-dimensional array of microphones closely coupled to the head, unproved signal strength is obtained as well as better localization within three dimensions. A sound output may be provided for diagnosis as information to the patient, or for comparison against the library of sounds collected by this apparatus and associated with particular clinical findings, More specifically, in one embodiment, the invention provides a clinical apparatus for measurements of sounds generated within the head including a set of microphones for receiving audio vibrations to generate corresponding electrical signals and a head fixture for supporting the microphones in contact with the patient's head at a set of predetermined locations dispersed in three dimensions. A signal processing circuit receives the electrical signals from the microphones when the microphones are applied to a patient's head using the head fixture to combine the electrical signals for isolating sound generated in a predetermined, region of interest within a patient's head and oat put ting an audio representation of the isolated sound.

It is a feature of at least one embodiment of the invention to provide improved diagnosis of clinical symptoms associated with head-originated sounds by permitting 3-D localization and isolation of those sounds. It is a feature of at least one embodiment of the invention to provide improved sensitivity and noise rejection through the combination of signals from multiple microphones.

The head fixture may position the microphones in simultaneous contact with the right and left side of the head and above the car canal, It is a feature of at least one embodiment of the invention to permit separation of anterior and posterior located sound sources.

The head fixture may position microphones on the head and neck.

It is a feature of at least one embodiment of the invention to provide improved superior and inferior localization of head and neck located sound sources.

The head fixture may provide elastic members interconnecting the microphones in a network that may conform to the head, It is a feature of at least, one embodiment of the invention to provide a lightweight fixture that permits patient mobility for studies that require patient movement while ensuring good microphone contact. It is a feature of at least one embodiment of the invention to provide a system that equalizes the pressure or; the microphones for uniform detection.

The microphones may include a first microphone element having a primary axis of sensitivity directed toward a patient's head as held on the head fixture and a second microphone having a primary axis of sensitivity directed away from the patient's head and wherein the signal processing circuitry combines the signals to reject external sound in favor of sound emanating from the patient's head;

It is a feature of at least one embodiment of the invention to enhance the detection of faint intracranial signals in the presence of outside ambient noise. It is another feature of at least one embodiment of the invention to permit use of the invention in a normal clinical environment permitting communication between the patient and clinician.

The microphone elements may include acoustic impedance-matching dements positioned between the microphone elements and a point of contact between the microphones and the patient's head.

It is a feature of at least one embodiment of the invention to improve the coupling between the microphones and the patient's head by limiting the impedance mismatch of an air layer. It is a further object of the invention to provide a coupling system that may work through the patient's hair.

The region of interest may be a subset of the volume of the head, and the signal processing circuit may further receive input from a user defining the region of interest within a volume of the user's head.

It is a feature of at least one embodiment of the invention to permit clinician-selected regions of interest for analysis thereby enlisting the clinician's training in assisting in the discrimination and localisation of sound sources. For example, sound sources that may be difficult to localize may be better localized by moving the region of interest while the clinician listens and compares changes in the sounds.

The clinical apparatus may include a display providing a three-dimensional representation of a human head and wherein the signal processing circuit displays the region of interest within that representation.

It is a feature of at least one embodiment of the invention to provide a simple and intuitive interface for localizing sounds in three dimensions.

The signal processing circuit may operate to phase shift the signals from the different microphones based on a calculated acoustic delay between the region of interest and the microphone and then To combine the phase shifted signals to produce the isolated sound. It is a feature of at least one embodiment of the invention to provide advanced isolation beyond that which can be produced by a single stethoscope moving over the surface of the patient's head in which isolation relies on differences in volume. The phase isolation technique allows collective information from the microphones to be used as well as the individual microphone signals.

The clinical apparatus of claim 1 wherein the set of microphones or separate set of audio transducers provide acoustic output phased for destructive and constructive interference to focus sound in the region of interest.

It is thus a feature of at least one embodiment of the invention provide for "contrast enhancement" or augmentation or cancellation of head or neck origins sounds by applying a directed external source of sound via ultrasound audio sound to a focus location within the patient's head.

The calculated acoustic delay may employ a model of the human head providing multiple materials with different sound speeds.

It is a feature of at least one embodiment of the invention to provide a more sophisticated localization that makes use of a priori knowledge about the anatomy of the human head.

The three-dimensional representation of the human head may be constructed of a data set from an imaging modality selected from the group consisting of CT PET ultrasound, and MRI.

It is a feature of at least one embodiment of the invention to tailor the localization calculation to the precise anatomy of the given patient.

The clinical apparatus may include a display wherein the signal processing circuit further operates to autocorrelate sounds received by the microphone to provide an identification of sound origin within three dimensions of the human head.

It is a feature of at least one embodiment of the invention to permit auto-localization of sounds through a correlation technique, providing a global assay of sound sources within the head.

The display may provide a three-dimensional representation of a human head and the signal processing circuit may display the sound origin within that representation.

It is a feature of at least one embodiment of the invention to provide a display of sound origins within the human head.

The invention may allow a step of comparing the output sound to a library of recorded sounds for diagnosis.

It is a feature of at least one embodiment of the invention to permit isolated sounds to be used for the purpose of diagnosis.

These particular objects and advantages may apply to only some embodiments falling within the claims and thus do not define the scope of the invention.

DETAILED DESCRIPTION OF THE PREFERRED EMBODIMENT

Figure 1:
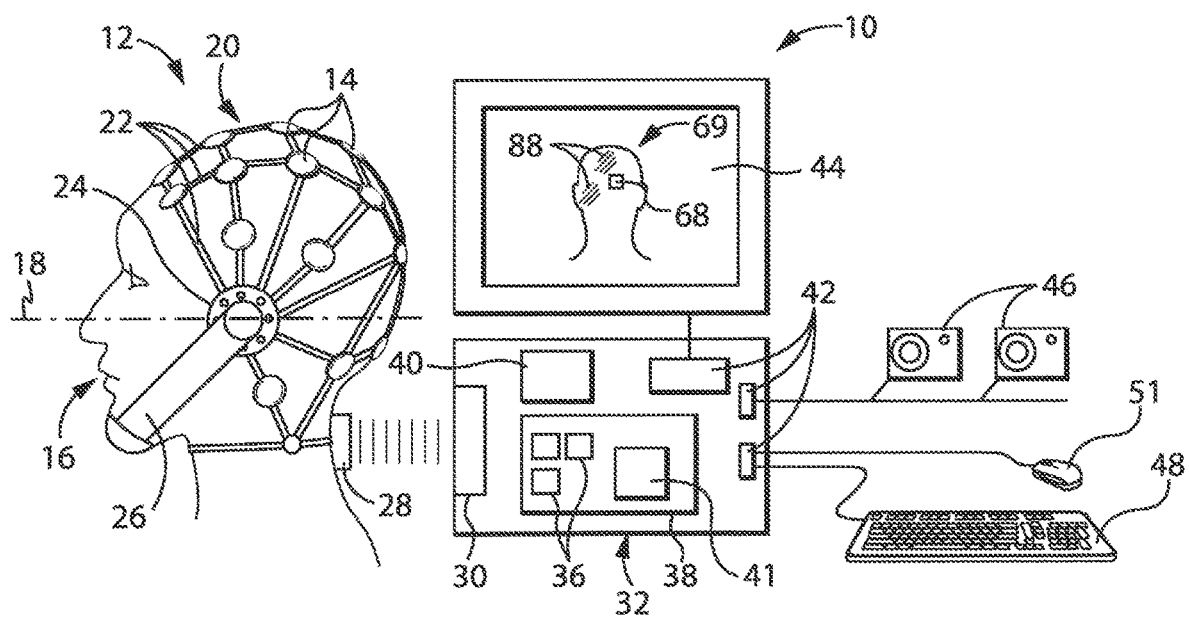
FIG. 1 is a block diagram of the principal components of the present invention showing a microphone army of microphones held by a head fixture for contacting multiple locations about the patient's head dispersed in three dimensions, the microphones communicating with a signal processing circuit for isolating and identifying intracranial sound sources and providing a display and audio output.

Referring now to FIG. 1. the clinical system 10 of the present invention may provide for a head mounted microphone array 12 providing a set of microphone assemblies 14 spaced in three dimensions over the surface of a patient's head 16 both above and below a level 18 of the ear canal on the left and right side of the patient's head 16. Only the left side of the patient's head 16 Is shown; however, the pattern on the left and right sides of the patient's head 16 will normally be mirror Images of each other. In one embodiment, most of the microphone assemblies 14 are positioned proximate to the patient's head 16; however, some microphone assemblies may be positioned on the patient's neck.

The microphone assemblies 14 are supported by a head fixture 20 comprised of a network of flexible cords 22 interconnecting the microphone assemblies 14 as the vertices in the network. The cords 22 are ideally sound dampening, so as to prevent communication of sound between the microphone assembly 14, and slightly elastic so that the network of cords 22 may conform closely to the patient's head 16 to the microphone assemblies 14 contacting the patient's skin with a slight normal force that is equalized by the cords 22. The cords 22 may be hollow to support electrical conductors that are in for communication of signals to a central location as will fee described.

In one embodiment, ends of some of the cords 22 may be joined at an earpiece 24 allowing the length of the cords 22 to extend radially therefrom and to be adjusted in length or tension, for example, by sliding through a spring-loaded cinching device or the like. The earpiece 24 may be counter tensioned by means of a chinstrap 26 engaging the patient's chin to provide a countervailing force to the force exerted by the cords 22 extending radially rearwardly and upwardly from each earpiece 24.

Signals from the microphone assembly 14 may be connected by shielded wires to a wireless transceiver 28 receiving those signals and transmitting them to a corresponding transceiver 30 on a signal processing unit 32. Preferably the wireless transceiver 28 is battery-powered to provide greatest flexibility to the patient.

The signal processing unit 32, for example, may receive the transmitted signals from the wireless transceiver 28, for example, in digitized form as multiple channels of audio data in real time and may store this data as one or more data files 36 in a computer memory 38. The data files 36 will be processed by a processor system 40 such as a multicore microprocessor communicating with the memory 38 and executing a stored program 41 contained therein as will be discussed below.

The signal processing unit 32 may further provide interface circuits 42 for high-speed generation of graphic images on a display 44 (for example, using a GPU card) as well as audio output circuits connected to speakers 46 or headphones or the like. The signal processing unit 32 may further communicate with and receive user commands, for example, through a keyboard 48 or mouse 51 or other cursor control device of a type known in the art.

Figure 2:
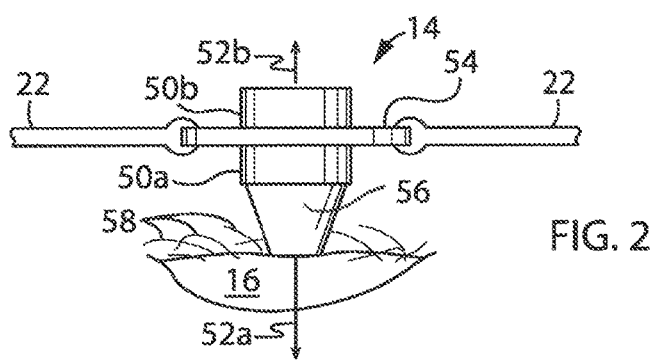
FIG. 2 is a side elevational view of a single microphone of FIG. 1 incorporating two opposed microphone elements.

Referring now to FIG. 2. each microphone assembly 14 may provide for two different microphone elements: a first element 50*a* having an axis of sensitivity 52*a* that will be directed toward the patient's head 16 and the second microphone element 50*b* generally having an axis of sensitivity 52*b* opposite in direction to axis of sensitivity 52*a*. These two microphone elements are acoustically isolated from each other and will be used for noise cancellation in which environmental noises outside of the patient's head 16 received by microphone element 50*b* are subtracted from intra-cranial sounds received by microphone element 50*a*. Each of the microphone elements 50*a* and 50*b* maybe audio microphones, for example, using piezoelectric elements and may include individual preamplifier circuits and other initial processing circuitry such as automatic gain control and the like.

The microphone elements 50*a* and 50*b* may be supported on an outrigger disk 54 attached to the cords 22 to provide improved resistance against torsion on the microphone elements 50*a* and 50*b* such as may cause the microphone axis of sensitivity 52*a* to be tipped from an orientation normal with respect to a surface of the patient's head 16.

An impedance-matching elastomeric extension 56 may communicate between the patient's head 16 and microphone element 50*a* to provide acoustic impedance matching between sound emanating from the patient's head 16 and the microphone element 50*a* for improved acoustic coupling. A tip of the elastomeric extension 56 may be tapered to a rounded point for direct contact with the patient's skin through hair 58.

Figure 3:
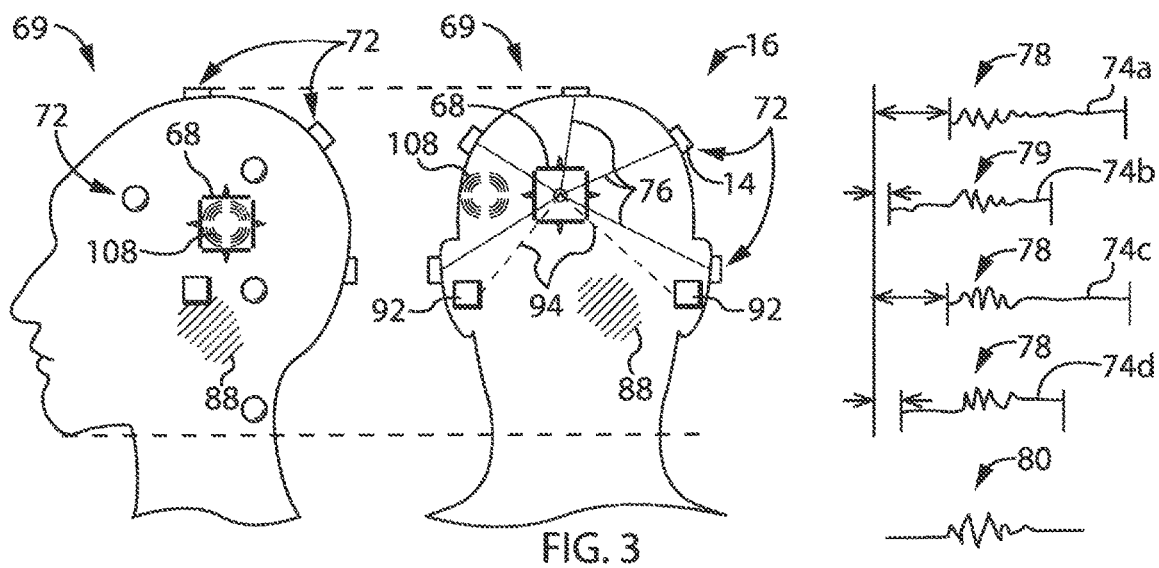
FIG. 3 is an example representation of a display generated by the signal processing circuitry of FIG. 1 allowing three-dimensional positioning of a region of interest within the volume of the patient's head and a corresponding isolation of correlated sounds based on that region of interest.
Figure 4:
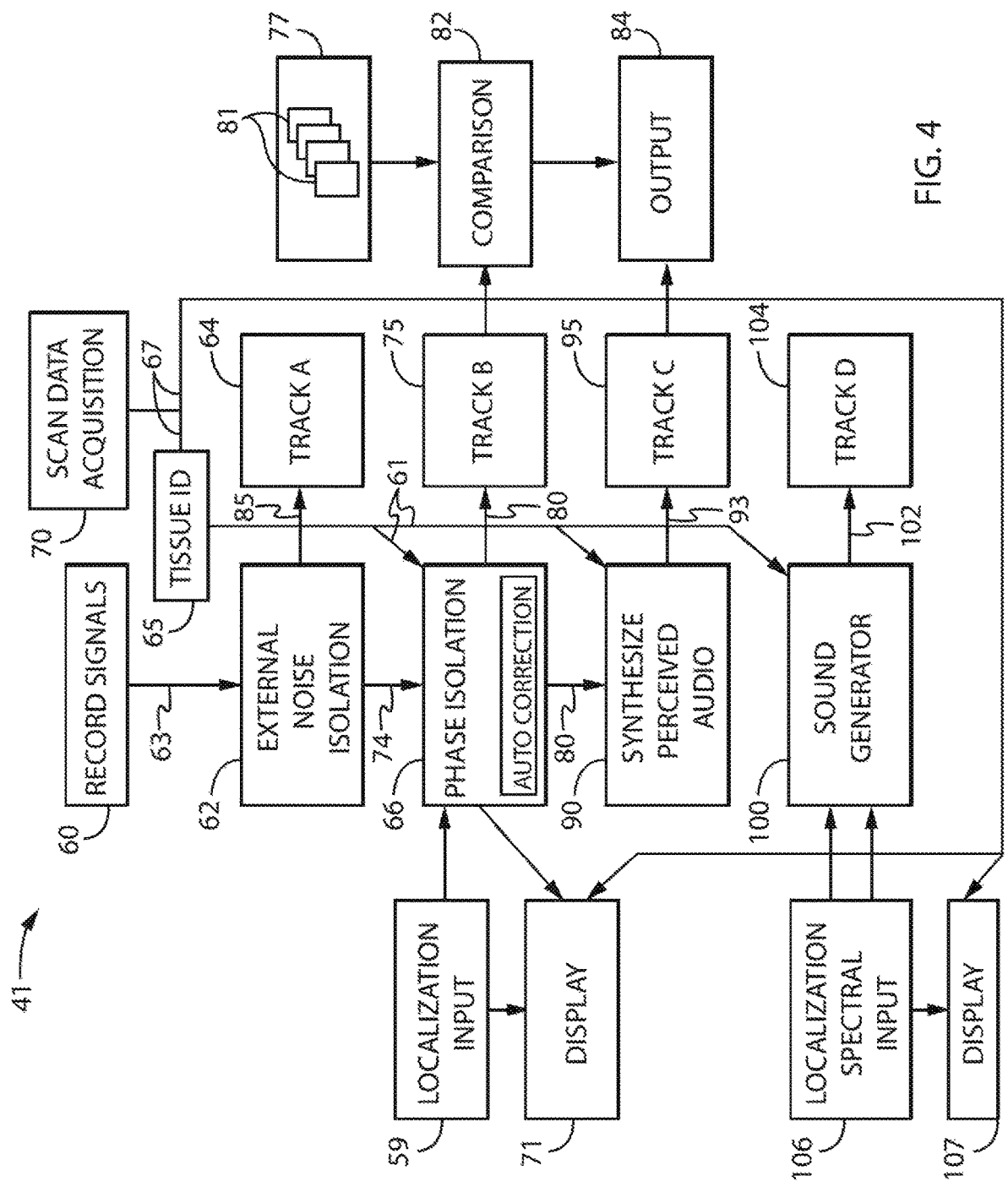
FIG. 4 is a functional block diagram of the signal processing circuitry.

Referring now to FIGS. 3 and 4, program 41 may operate initially, as indicated by process block 60, to record original signals 63 from each of the microphone assemblies 14. The original signals 63 may include individual signals from microphone elements 50*a* and 50*b*, or may be the combined signals from microphone elements 50*a* and 50*b* performed by the microphone assemblies 14 to better eliminate phase shift in the noise cancellation process.

At process block 62, recorded original signals 63 are initially processed to separate intracranial sound sources from environmental sounds. This processing may employ a variety of techniques including, for example, subtracting the signal received from microphone element 50*b* (assumed to contain only environmental noise) from the signal obtained from microphone element 50*a*. For this purpose, the signal from microphone element 50*b* may be scaled before subtraction to minimize the total acoustic energy of the subtracted signals thereby optimizing the cancellation effect. Other sound cancellation techniques may be used to make use of the fact that external noise sources are relatively removed from the patient's head and thus may have similar phase as received by each microphone element 50*b* allowing the sounds to be identified and subtracted from the signals from microphone elements 50*a*. In addition or alternatively, process block 62 may make use of frequency-selective filters and may operate to remove regular acoustic or electrical noise, for example, 60 cycle hum, through the use of adaptive filtering as is generally known in the art.

Process block 62 produces a noise-reduced signal 74 largely limited to intracranial acoustic sources but also provides an environmental sound signal 85 (for example, isolated from microphone elements 50*b*) alone representing the external environment which maybe output as Track A and stored as indicated by process block 64. This Track A may be used, for example, to allow a clinician's instructions to the patient, for example, instructing the patient to perform a predetermined set of motions to help identify intracranial noises, to be reviewed in parallel with the noise reduced signal 74, as synchronized with this noise reduced signal and other tracks to be produced, for the purpose of associating intracranial sounds, for example, with head movements or the like.

Referring to FIGS. 1, 3 and 4, the noise-reduced intracranial signals 74 are then processed by a phase isolator indicated by process block 66. This phase isolator may make use of localization information (per process block 59) describing a particular region of interest 68 in the patient's head 16 (shown in FIG. 3). The region of interest 68 defines the location from which sound might be emanating and accordingly, a region kin which sound is preferentially to be acquired isolated from sounds from other regions. The location information defining the region of interest 68, for example, may be input using the mouse 50 to move a representation of a region of interest 68 over a three-dimensional representation of the patient's head 16 on display 44. As depicted, one implementation of a three-dimensional representation 69 is obtained through aligned front elevational and side elevational images of the patient's head 16, with separate cursors tracking region of interest 68 in each view. However it will be appreciated that other three-dimensional rendering techniques may be employed including, for example, a single display of a rotatable model.

The three-dimensional representation 69 in detail may provide a standard template of a typical head; however, in one embodiment, the three-dimensional representation 69 maybe derived from actual image data 67 of the patient's head obtained through another modality such as CT (computed tomography), MRI (magnetic resonance imaging), ultrasound or PET (positron emission tomography) scanning as indicated by process block 70. This data may then be displayed with a properly scaled and located representation of the region of interest 68 together with other output data which will be described below.

Microphone locations 72 of the microphone assemblies 14 may be depicted on the three-dimensional representation 69 to enable the clinician to confirm the proper location of the microphone assemblies 14 on the patient's head 16 as registered to the three-dimensional representation 69. Ideally the microphone assemblies 14 are placed in standard locations based on standard anatomical references on the patient's head 16; however, the program 41 may accommodate a manual repositioning of the microphone locations 72 to conform to actual measurements made on a given patient as indicated by process block 71. The positioning of these microphone locations 72 helps establish correspondence between the displayed image and the acquired data. Information about the location of the region of interest 68 and the microphone locations 72 is provided to the phase isolation task of process block 66.

Based on the location of the region of interest 68 and the microphone locations 72 of the microphone assemblies 14, noise reduced signals 74 (for example, signals 74*a*-74*d*) associated with each microphone assembly 14 may be shifted in time with respect to each other according to the acoustic distance 76 between the microphone assembly 14 receiving the signal 74 and a center of the region of interest 68. The acoustic distance 76, in the simplest case, may be a geometric distance between the microphone locations 72 and the center of the region of interest 68; however, the invention contemplates that the differences in the materials' properties within the patient's head 16 will be modeled so that the acoustic distance 76 is modified by the sum of the sound speeds in the different materials of the skull, brain, cerebral fluid and the like, along a line between the microphone locations 72 and the center of the region of interest 68 for each microphone assembly 14.

In one embodiment, the acoustic distance 76 may make use of actual image data 67 taken at process block 70. This image data 67 is segmented per process block 65 to identify a tissue type linked to the empirically determined acoustic properties of the different types of tissues. This in ion-nation 61 is then provided to the phase isolation of process blocks 66 so that acoustic distance 76 may closely model the acoustic distances unique to a patient.

It will be appreciated that the phase shifting of the signals 74a-74d according to acoustic distance 76 will be such as to align signal portions 78 originated within the region of interest 68 (and to unaligned signals received from other regions) allowing an isolated signal 80 to be generated as an ensemble average having improved signal strength, rejection of uncorrected noise, and rejection of sounds outside of the region of Interest 68.

The resulting isolated signal 80 may be output as Track B and recorded as indicated by process block 75 and represents an output of a virtual stethoscope placed directly on the region of interest within the patient's head, something that, would be impossible with an ordinary stethoscope. The isolated signal 80 presents the acoustic signals from the region of interest 68 isolated from other acoustic signals elsewhere in the patient's head 16. The isolation combines signals from multiple microphone assemblies 14 to preferentially increase the strength of the signals emanating from the region of interest 68 above the signals emanating outside of the region of interest, as a function of imputed location of the signals origin and in distinction from simply selecting the microphone with the largest signal amplitude, for example.

The recorded Track B may be routed over the speakers 46 or headphones to allow for the patient and clinician to hear the sound for the purpose of confirmation and diagnosis. In this regard, the invention contemplates that a library 77 of such recorded isolated signals 81 will be collected associated with particular diagnoses. These isolated signals 81 may be reviewed by the clinician or may be automatically compared to the isolated signal 80 as indicated by process block 82 to further the diagnosis process. In addition, each isolated signal 81 of the library 77 may be associated not only with a diagnosis but also with a particular location of the head, for example, associated with different portions of cerebral vasculature, to improve the correlation process by informing the matching process both with the actual isolated signal 81 and the location from which that isolated signal 81 may be independently matched to corresponding data for the recorded Track B.

The results of this comparison of process block 82 may be output as indicated by process block 84 both, quantitatively, to the display 44 (indicating a degree of matching and the associated data on the matching isolated signal 81) and to the speakers 46 providing both the isolated signal 80 and isolated signal 81 for independent consideration by the clinician.

At process block 66, a correlation 86 may also be performed for episodic sounds such as clicks or pops where signal portions 78 may be identified automatically and correlated independent of knowledge of the location of the sounds. When this feature is invoked, the region of interest 68 is expanded to the entire volume of the head 16 and the shifting of signals 74 is performed to align the episodic feature of the pop or click. In this case, the resulting correlation (the point of greatest correlation) is used to back derive the location of the sound using the acoustic distances 76 revealed in the necessary shifting between the signals 74 (effectively reversing the process described above). The result is that the location of the click or pop may be determined as manifest in a three dimensionally located shading 88 placed on the three-dimensional representation 69. This process avoids the need for an independent identification of a region of interest 68. The shading 88 may, in one embodiment, be animated in time with the popping and clicking recorded on Track B to help distinguish multiple sound sources visually while the sound is being played.

As indicated by process block 90, the phase-isolated signal 80 may be further processed to better approximate any sound which, would be heard by the patient at the patient's inner ear regions 92. The synthesis process may, for example, model the attenuation at multiple frequencies expected through intervening tissue along paths 94, the latter, for example, determined using the tissue information 61 (providing tissue type acoustic properties and tissue locations) as extracted at process block 65. The result is a Track C that may be recorded at process block 95 to be played back to the patient, as indicated by process block 84, for confirmation that the identified sound is in fact the sound being heard by the patient. This process may, for example, adjust the volume and frequency content of Track B independently for each ear region 92.

It will be appreciated that each of the microphone assemblies 14 may be augmented to emit as well as detect audio signals, for example, by combining the microphone assemblies 14 with a special audio transducer or using the microphone elements 50a themselves as audio output devices. As indicated by process block 100, the ability to generate sound signals at each microphone assembly 14 allows signals 102 to be input into the patient's head 16 as Track D indicated by process block 104. The sound signals may be constructed to provide constructive and destructive interference to effectively focus the generation of the sound to a region of interest 68 within the patient's head as if the sound were emanating from that location. In addition, the sounds may be impressed on an ultrasonic carrier that makes use of nonlinearities in the tissue to demodulate modulate at audible frequencies. This process employs the reverse phasing adjustment of signals 102 from each of the microphone assemblies 14 to the phasing adjustment of the signal 74 from the microphone assemblies 14. The particular spectral content or wave shape of the signals 102 and their desired location within the region of interest 68 may be set as indicated by process block 106 using a cursor system 108 similar to the cursor depicting the region of interest 68 for identifying the location of the sound source indicated by process block 107.

A variety of different spectral characteristics can be obtained, for example, by selection of waveform type (square wave, sine wave) or frequency, or by defining a power spectrum of the waveform through an inverse Fourier transform. This generated waveform, being a combination of signals 102, may be used to help the patient identify the perceived location of the sound source (by manipulating the region of interest 68 through the patient's head) or for the development of a canceling or masking signal that can subjectively help the patient to mask or ignore the tinnitus.

It is possible that the generation of the sound source can also be used to train the patient to minimize subjective tinnitus.

The present invention is primarily related to recording and processing audio signals generally in the range of human hearing or within the range of approximately 100-15000 but is not intended to be limited to this range unless otherwise noted.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What I claim is:

1. A clinical apparatus for measurements of sounds generated within a patient's head or transmitted from a neck or body comprising:
    a set of microphones for receiving audio vibrations to generate corresponding electrical signals;
    a head fixture for supporting the set of microphones in contact with the patient's head at a set of predetermined locations dispersed in three dimensions;
    a signal processing circuit receiving the electrical signals from the set of microphones when the set of microphones are applied to the patient's head using the head fixture to combine the electrical signals for isolating sound generated in a selected region of interest of multiple selectable regions within the patient's head less than an entire volume of the patient's head, the isolated sound being sound isolated from sounds emanating outside of the selected region of interest through a phase cancellation process;
    a display providing an output to an operator identifying a location of the selected region of interest; and
    an audio transducer receiving the isolated sound and outputting the isolated sound from the selected region of interest to be perceptible as sound by a human.

2. The clinical apparatus of claim 1 wherein the head fixture positions the set of microphones in simultaneous contact with right and left sides of the patient's head and above an ear canal of the patient's head.

3. The clinical apparatus of claim 2 wherein the head fixture positions the set of microphones on the head and neck.

4. The clinical apparatus of claim 1 wherein the head fixture provides elastic members interconnecting the set of microphones in a network that may conform to the patient's head.

5. The clinical apparatus of claim 1 wherein the microphones include a first microphone element having a primary axis of sensitivity directed toward the patient's head as held on the head fixture and a second microphone having a primary axis of sensitivity directed away from the patient's head and wherein the signal processing circuitry combines the electrical signals to reject external sound in favor of sound emanating from the patient's head.

6. The clinical apparatus of claim 1 wherein the set of microphones include acoustic impedance matching elements positioned between the set of microphones and a point of contact between the set of microphones and the patient's head.

7. The clinical apparatus of claim 1 wherein the selected region of interest is a subset of a volume of the patient's head and wherein the signal processing circuit further receives input from a user defining the selected region of interest within the volume of the patient's head.

8. The clinical apparatus of claim 7 further including a display providing a three-dimensional representation of a human head and wherein the signal processing circuit displays the selected region of interest within that representation.

9. The clinical apparatus of claim 8 wherein the signal processing circuit operates to phase shift the electrical signals from the set of microphones based on a calculated acoustic delay between the selected region of interest and the set of microphones and then to combine the phase shifted signals to produce the isolated sound.

10. The clinical apparatus of claim 9 wherein the calculated acoustic delay employs a model of the human head providing multiple materials with different sound speeds.

11. The clinical apparatus of claim 10 wherein the three-dimensional representation of the patient's head is constructed of a data set from an imaging modality selected from a group consisting of CT, ultrasound, and MRI.

12. The clinical apparatus of claim 1 further including a display wherein the signal processing circuit further operates to autocorrelate sounds received by the set of microphones to provide an identification of sound origin within three-dimensions of the patient's head.

13. The clinical apparatus of claim 12 further including a display providing a three-dimensional representation of a human head and wherein the signal processing circuit displays the sound origin within that three-dimensional representation.

14. The clinical apparatus of claim 1 wherein the set of microphones or separate set of audio transducers provide acoustic output phased for destructive and constructive interference to focus sound in the selected region of interest.

15. A method of clinical measurements of sounds generated within a patient's head employing:
   a set of microphones for receiving audio vibrations to generate corresponding electrical signals;
   a head fixture for supporting the set of microphones in contact with the patient's head at a set of predetermined locations dispersed in three dimensions; and
   a signal processing circuit receiving the electrical signals from the set of microphones when applied to the patient's head using the head fixture to combine the electrical signals for isolating sound generated in a selected region of interest of multiple selectable regions within the patient's head less than an entire volume of the patient's head, the isolated sound being sound isolated from sounds emanating outside of the selected region of interest through a phase cancellation process, outputting to an operator a location of the selected region of interest, and outputting an audio representation of the isolated sound from the selected region of interest to be perceptible as sound by human, the method comprising:
   (a) positioning the head fixture and the set of microphones on the patient's head;
   (b) acquiring electrical signals from the set of microphones during a predetermined activity by the patient;
   (c) processing the electrical signals on the signal processing circuit to isolate sounds from the selected region of interest less than an entire volume of the patient's head within the patient's head, the isolated sound being sound isolated from sounds emanating outside of the selected region of interest through the phase cancellation process;
   (d) displaying an output to the operator identifying the location of the selected region of interest; and
   (e) outputting the isolated sounds from the selected region of interest from the predetermined region using an audio transducer presenting the isolated sound in a form perceptible as sound by a human for clinical diagnosis of patient perceived intracranial sounds.

16. The method of claim 15 wherein the head fixture positions the set of microphones in simultaneous contact with right and left sides of the head and above an ear canal of the patient's head.

17. The method of claim 16 wherein the head fixture positions the set of microphones on the patient's head and neck.

18. The method of claim 15 wherein the head fixture provides elastic members interconnecting the set of microphones in a network that may conform to the patient's head.

19. The method of claim 15 wherein the selected region of interest is a subset of the volume of the patient's head and further including a step of inputting location information from a user defining the location of the selected region of interest within a the volume of the patient's head.

20. The method of claim 19 further including a step of acquiring an image set of the patient's head using an imaging modality selected from a group consisting of CT, PET, ultrasound, and MRI and generating a model of acoustic properties of the patient's head for isolating the sound generated in the selected region of interest.

21. The method of claim 15 further including a step of comparing the isolated sounds to a library of recorded sounds for diagnosis.

* * * * *